United States Patent [19]

Swanson

[11] Patent Number: 4,645,505
[45] Date of Patent: Feb. 24, 1987

[54] WRIST IMPLANT

[76] Inventor: Alfred B. Swanson, 2945 Bonnell Ave., SE., Grand Rapids, Mich. 49506

[21] Appl. No.: 709,332

[22] Filed: Mar. 7, 1985

[51] Int. Cl.⁴ .............................................. A61F 2/42
[52] U.S. Cl. ........................................ 623/21; 623/18; 623/16
[58] Field of Search ....................... 623/21, 18, 19, 20, 623/16

[56] References Cited

U.S. PATENT DOCUMENTS 3,879,767  4/1975  Stubstad ................................. 623/21
3,987,500  10/1976  Schlein ................................... 623/21
4,131,957  1/1979  Bokros .................................... 623/18

Primary Examiner—Richard J. Apley
Assistant Examiner—Alan W. Cannon
Attorney, Agent, or Firm—Price, Heneveld, Cooper, DeWitt & Litton

[57] ABSTRACT

A wrist implant for stabilizing the proximal carpal row and preventing ulnar migration thereof includes a body having a generally planar, radial surface which has a teardrop shape defined by curvilinear dorsal and palmar lateral edges and a semicircular medial edge. The body further defines generally triangular or wedge-shaped dorsal and palmar surfaces which join to form a curved medial surface. The body defines a smooth, cup-shaped, concave recess including a lunate surface. The recess is configured to receive the carpal row lunate bone. The implant further includes a proximal stem which extends perpendicular to the radial surface. The implant is adapted to be positioned at the distal end of the radius with the stem inserted into the intramedullary canal of the radius bone. The implant constrains the proximal row of the carpal bones, stabilizing the joint and preventing ulnar migration of the wrist bones.

29 Claims, 9 Drawing Figures

WRIST IMPLANT

BACKGROUND OF THE INVENTION

The present invention relates to arthroplastic reconstruction of the human joints and more particularly to implant arthroplasty of the wrist joint.

In recent years, various implants have been successfully employed for the restoration of the joints of the hand and wrist affected with rheumatoid arthritis and similar conditions. Aseptic necrosis and/or arthritis of the carpal bones, either primary or secondary to trauma, is a frequent cause of disability of the wrist. Surgical treatment of conditions of the wrist have included intercarpal fusion, wrist fusion, local resection, proximal row carpectomy, bone grafting, radial styloidectomy, radial shortening or ulnar lengthening and soft tissue interposition arthroplasty.

The wrist is a key joint in the proper function of the hand. The wrist includes eight carpal bones arranged in rows of four each. The proximal row includes the pisiform, triquetrum, lunate and scaphoid bones. The distal row includes the hamate, capitate, trapezoid and trapezium bones. The distal end of the radius bone of the arm articulates with the scaphoid and lunate carpal bones. The distal end of the radius also articulates with the head of the ulna. The joints between the carpal bones and the joint between the carpals and the radius permit wrist and hand movement. Stability and mobility in the wrist are important for normal function of the extrinsic muscles of the fingers.

Rheumatoid arthritis is a frequent cause of severe wrist impairment. Such may affect the soft tissues and the joints of the wrist including the radiocarpal, intercarpal and radioulnar joints. The disease may result in loosening of the ligaments and erosive changes in the bones. This disturbs the multiple link system of the wrist joint. In severe cases, the wrist may become completely dislocated. Ulnar displacement of the proximal carpal row may result from loosening of the ligaments on the radial aspect of the joint. Radial deviation of the hand on the forearm may then result. Subluxation of the distal radioulnar joint associated with such deviation causes a loss of stability on the ulnar aspect of the wrist.

Various reconstructive procedures of a disabled wrist have heretofore been employed. These procedures include lunate and scaphoid implant arthroplasty using silicone rubber implants. The implants act as articulating spacers and maintain the relationship of adjacent carpal bones while preserving mobility of the wrist. Examples of such implants may be found in U.S. Pat. No. 4,164,793, entitled LUNATE IMPLANT and issued on Aug. 21, 1979 to the present inventor; and U.S. Pat. No. 4,198,712, entitled SCAPHOID IMPLANT and issued on Apr. 22, 1980 to the present inventor.

Wrist implant arthroplasty has been employed when instability of the wrist is caused by subluxation or dislocation of the radiocarpal joint. Radiocarpal joint implant resection arthroplasty has included resection of the lunate bone, part of the distal scaphoid, the capitate and the triquetrum bones, as well as the end of the radius and distal portion of the ulna. A double stem implant has been used with one stem inserted into the intramedullary canal of the radius and the other stem inserted in a channel reamed through the remnant of the capitate bone and the third metacarpal. In addition, an intramedullary stemmed, cuffed implant may be used to cap the resected distal ulna to preserve the anatomic relationships and physiology of the distal radioulnar joint following ulnar head resection.

SUMMARY OF THE INVENTION

In accordance with the present invention, a relatively rigid wrist implant is provided for stabilizing the proximal carpal row to restrict or prevent ulnar translation of the carpal bones. Essentially, the implant includes a body which defines a proximal surface. Spaced palmar and dorsal sidewalls extend perpendicular to the proximal surface. The sidewalls join to form an end wall. The end wall and sidewalls define a carpal recess dimensioned to receive a portion of the carpal row and prevent ulnar migration of the row.

In narrower aspects of the invention, the recess is undercut into the end wall and is dimensioned to receive the lunate bone of the proximal carpal row. The body is generally wedge-shaped in dorsal plan, and the proximal surface has a generally teardrop shape. The body further defines a proximal intramedullary stem dimensioned to be inserted into the intramedullary canal of the radius bone. In the preferred form, the implant is fabricated as a one-piece member from a medical grade titanium alloy or a medical grade superalloy based on nickel and/or cobalt and to which chromium is added. The implant constrains the carpal bones, stabilizes the wrist joint and causes wrist motion to occur at the midcarpal joint. In addition, the implant may provide a distal buttress and surface for an ulnar head implant or cap.

DETAILED DESCRIPTION OF THE PREFERRED EMBODIMENT

Figure 1:
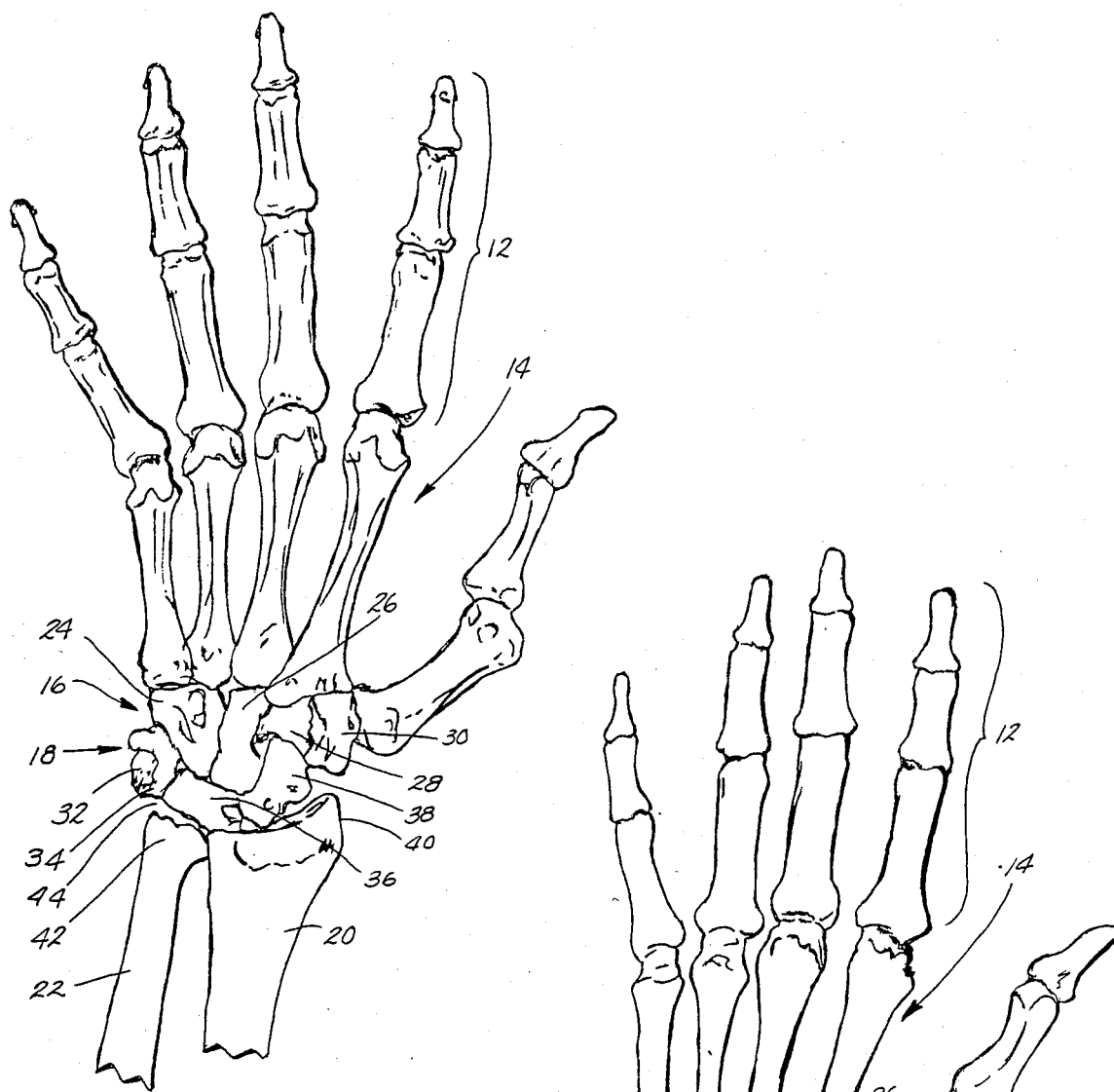
FIG. 1 is a fragmentary, dorsal view of the hand, wrist and distal portions of the ulna and radius.

With reference to the drawings, FIG. 1 illustrates a dorsal view of a hand and wrist. The hand includes phalanges 12, metacarpals 14, a distal carpal row 16 and a proximal carpal row 18. The proximal carpal row is adjacent the radius 20 and the ulna 22. The distal carpal row 16 includes the hamate 24, the capitate 26, the trapezoid 28 and the trapezium 30. The proximal carpal row includes the pisiform 32, the triquetrum 34, the lunate 36 and the scaphoid 38. The distal end of the radius 20 includes a styloid process 40. The distal end or head 42 of the ulna includes a styloid process 44. In the wrist illustrated in FIG. 1, the proximal carpal row 18 has migrated medially towards the ulna 22. The radiocarpal joint between the radius and the scaphoid and lunate has been affected and severe wrist impairment is present. Ulnar displacement of the proximal carpal row is typically the result of rheumatoid arthritis.

Figure 2:
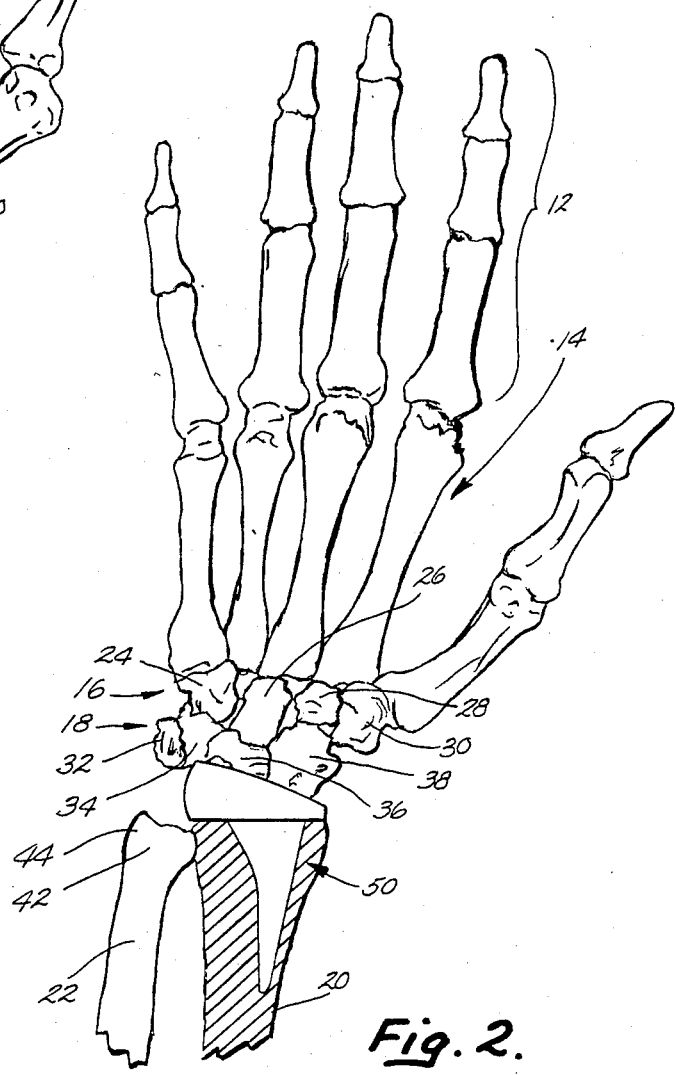
FIG. 2 is a fragmentary, dorsal view of the hand, wrist and distal portions of the radius and ulna showing a wrist implant in accordance with the present invention.
Figure 3:
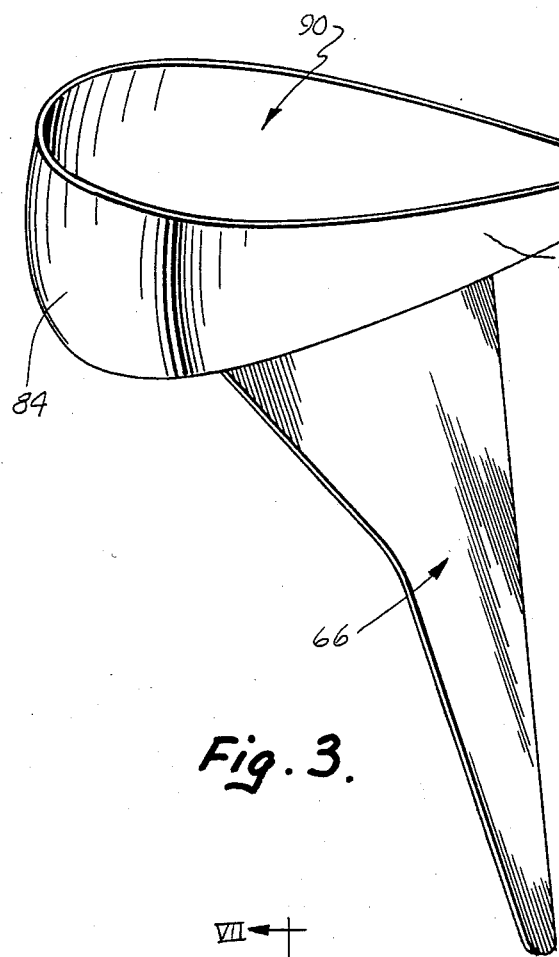
FIG. 3 is a perspective view of the implant.

In accordance with the present invention, a wrist implant generally designated 50 in FIG. 2 is provided to stabilize the proximal carpal row and constrain or prevent movement or ulnar displacement of the proximal row. As illustrated in FIG. 2, implant 50 is positioned between the distal end of the radius 20 and the proximal row 18 of the carpal bones. A portion of the radius 20 has been resected and implant 50 is positioned to receive or trap the lunate bone 36. Implant 50 in effect replaces the radiocarpal joint.

Figure 8:
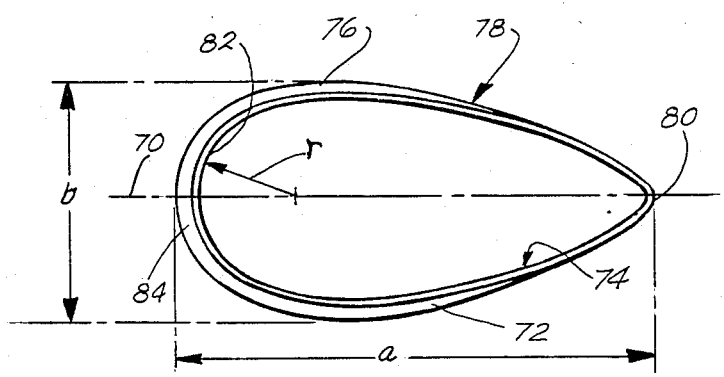
FIG. 8 is a view of the carpal surface of the implant.
Figure 9:
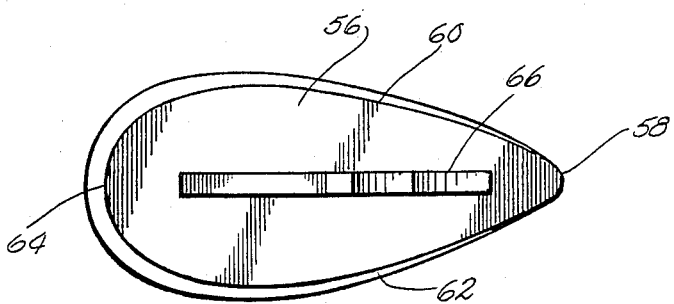
FIG. 9 is a view of the proximal surface or bottom of the implant.

As seen in FIGS. 3-9, implant 50 includes a body portion 52 and an intramedullary stem 54. Body portion 52 defines a proximal or bottom surface 56 (FIG. 9). Surface 56 has a generally teardrop shape and defines an apex 58, increasing radius, curved lateral or dorsal and palmar edges 60, 62, respectively, and a semicircular medial edge or base 64. Extending perpendicular to proximal surface 56 is an intramedullary stem 66. Stem 66 extends from a point generally centrally of surface 56. Stem 66 is an elongated, planar member having a rectangular cross section. Stem 66 tapers from surface 56 to an apex or point 68. As shown in FIG. 2, stem 66 is dimensioned to extend into the intramedullary canal of radius 20.

Figure 4:
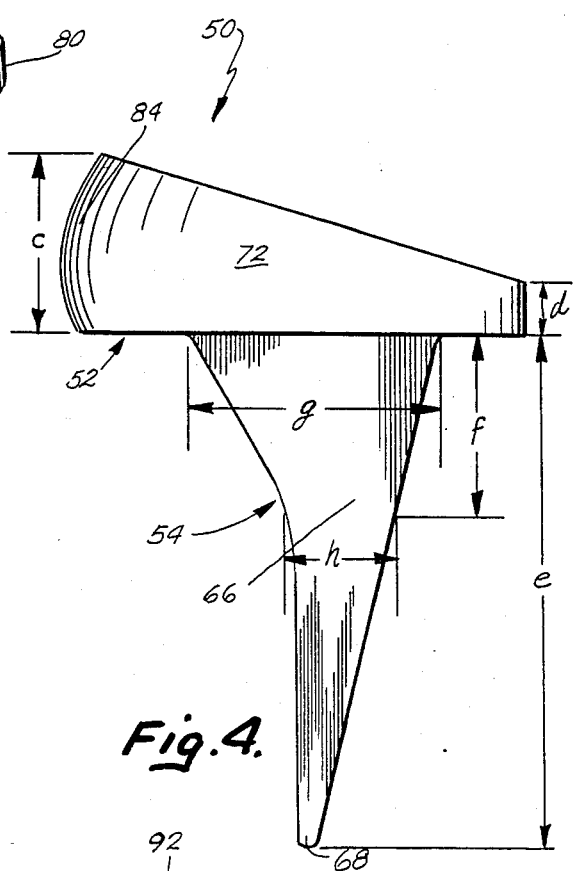
FIG. 4 is a dorsal view of the implant.
Figure 5:
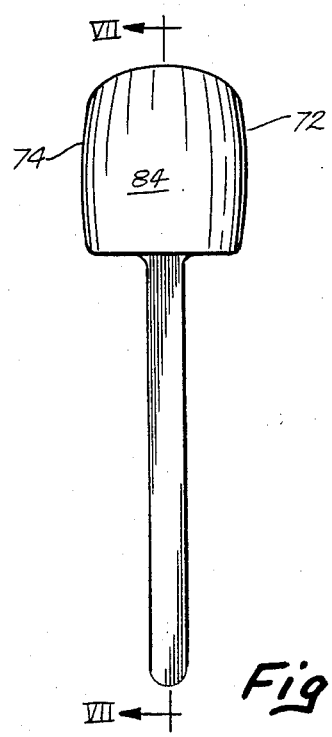
FIG. 5 is a medial end view of the implant.
Figure 6:
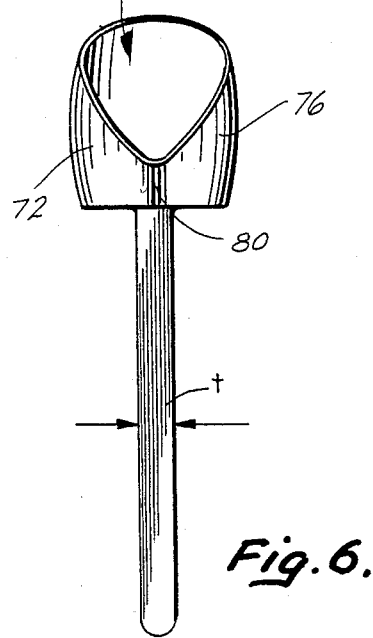
FIG. 6 is a lateral end view of the implant.
Figure 7:
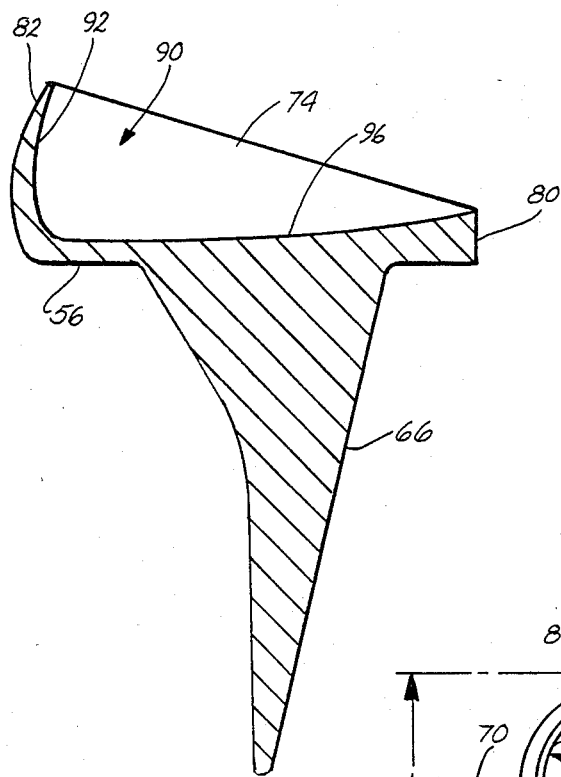
FIG. 7 is a cross-sectional view taken generally along line VII—VII of FIG. 5.

Body portion 52 is symmetrical about an axis 70 (FIG. 8). Body portion 52 includes a dorsal surface 72 defined by a sidewall 74 and a palmar surface 76 defined by a sidewall 78. Walls 74, 78 taper outwardly from an apex or lateral end 80. Walls 74, 78 join medially to define a medial end wall 82 having a surface 84. Surfaces 72, 76, as seen in FIG. 4, are generally triangular or wedge-shaped in plan. The sidewalls and end walls of portion 52 define a carpal recess 90. Recess 90 has a generally U-shaped or semicircular cross section in a plane perpendicular to axis 70. Recess 90 tapers from the medial wall 82 towards the apex 80. Recess 90 is undercut at wall 82 to define a lunate surface 92. Recess 90 is configured so that lunate bone 36 is substantially disposed within the recess and partially encircled. The ulnar surface of the lunate abuts surface 92 of recess 90. Scaphoid 38 is also partially received within recess 90, as shown in FIG. 2. The proximal surfaces of the lunate and scaphoid bones will contact the curved base or bottom wall 96 of recess 90. The cup-shaped body portion 52 and the surfaces of recess 90 define a radiocarpal joint. Due to the configuration of the recess, the lunate bone and hence the proximal carpal row are in effect locked or constrained from moving toward the ulna 22. Movement of the carpal row is prevented. Wrist movement will shift to the midcarpal joint. Although movement is restricted, the wrist is stabilized and the pain associated with ulnar displacement of the carpal row is reduced or substantially eliminated.

It is presently preferred that the implant 50 be fabricated as a precision casting in a conventional fashion from titanium or a medical grade superalloy based on nickel and/or cobalt to which chromium is added for oxidation resistance. Such superalloys are well known in this industry. One such alloy is sold under the brand designation Vitallium. It is preferred that a plurality of implants of graduated size be provided to insure a stable fit with individual patients. Each of these implants would be graduated and have the same general proportions as the preferred embodiment illustrated. The principal concern is to provide a cup-shaped recess to constrain or restrict ulnar translation of the carpal bones.

Also, should the head of the ulna be resected and a cap implant provided, implant 50 could provide a distal buttress and surface for the ulna head implant. As clearly seen in FIG. 2, with the implant in position and the ligamentous structures repaired, the proximal carpal row is held in its proper relationship to the distal end of the radius.

In an existing embodiment of the wrist implant in accordance with the present invention, body portion 52 has an overall longitudinal dimension "a" of approximately 1.30 inches and an overall width dimension "b" of approximately 0.625 inch, as indicated in FIG. 8. Medial surface 84 has an overall height "c" of approximately 0.475 inch, and apex 80 has an overall height "d" of 0.150 inch, as indicated in FIG. 4. The distal edge of medial wall 82 has a radius "r" of approximately 0.20 inch, as shown in FIG. 8. Stem 66 has an overall length designated "e" in FIG. 4 of approximately 1.4 inches. Stem 66 has an overall transverse dimension designated "g" at the proximal surface 56 of approximately 0.70 inch. Stem 66 tapers to an overall transverse dimension designated "h" (FIG. 6) of approximately 0.30 inch at a distance "f" of approximately 0.50 inch from the proximal surface. Recess 90 has a highly polished or smooth finish and is cupped to conform generally to the exterior proximal surfaces of the lunate and scaphoid bones. Stem 66 has a thickness designated "t" (FIG. 6) of approximately 0.10 inch.

The wrist implant in accordance with the present invention is easily and relatively inexpensively manufactured using conventional fabrication techniques from suitable medical grade, high strength and wear resistant metals. A relatively simple surgical procedure may be employed to repair the wrist and prevent ulnar migration of the carpal row. This results in increased stability and freedom from pain.

The above description should be considered as that of the preferred embodiment. The true spirit and scope of the present invention may be determined by reference to the appended claims.

The embodiments of the invention in which an exclusive property or privilege is claimed are defined as follows.

1. A wrist implant for stabilizing the proximal carpal row and preventing ulnar migration thereof, said implant comprising:
   a rigid body defining a generally planar, radial surface having a generally teardrop shape and including an apex, curvilinear dorsal and palmar lateral edges and a semicircular medial edge;
   a generally triangular-shaped dorsal surface having a truncated apex and extending distally from the dorsal edge of said radial surface;
   a generally triangular-shaped palmar surface having a truncated apex and extending distally from said palmar edge of said radial surface, said dorsal surface and said palmar surface joining to form a curved medial surface; and
   a carpal surface defining an elongated, smooth, cup-shaped, concave recess including a lunate surface, said recess configured and dimensioned to receive, at least partially encircle and constrain the carpal row lunate bone.

2. A wrist implant as defined by claim 1 further including:
   a proximal stem extending generally perpendicular to said radial surface.

3. A wrist implant as defined by claim 1 wherein said recess is undercut towards said medial surface of said body.

4. A wrist implant as defined by claim 2 wherein said recess is undercut towards said medial surface of said body.

5. A wrist implant as defined by claim 2 wherein said proximal stem is an elongated, generally planar member having a rectangular cross section.

6. A wrist implant as defined by claim 5 wherein said stem tapers from said radial surface to a proximal free end.

7. A wrist implant as defined by claim 4 wherein said proximal stem is an elongated, generally planar member having a rectangular cross section.

8. A wrist implant as defined by claim 7 wherein said stem tapers from said radial surface to a proximal free end.

9. A wrist implant as defined by claim 1 wherein said body is fabricated from metal.

10. A wrist implant as defined by claim 9 wherein said metal is titanium.

11. A wrist implant as defined by claim 10 wherein said metal is a superalloy.

12. An implant for preventing shift in the ulnar direction of the proximal carpal row which includes the lunate, said implant comprising:
a one-piece body having a generally wedge shape in dorsal plan view, said body defining a generally triangular-shaped proximal surface having a semicircular base and curved sides joining in an apex, said body further defining a pair of spaced palmar and dorsal sidewalls extending perpendicular to said proximal surface and joining to define a generally curved end wall, said sidewalls and end wall defining an elongated, smooth, cup-shaped, concave carpal recess including a lunate surface, said recess and lunate surface configured and dimensioned to receive, enclose and constrain the carpal row lunate and prevent ulnar migration of said row.

13. An implant as defined by claim 12 wherein said recess is generally U-shaped in transverse cross section.

14. An implant as defined by claim 13 wherein said recess tapers from said end wall towards said apex.

15. An implant as defined by claim 14 wherein said recess is undercut into said end wall to restrict proximal movement of the carpal bone disposed in said recess.

16. An implant as defined by claim 12 wherein said one-piece body further defines an elongated, generally flat, intramedullary stem extending generally perpendicular from said proximal surface.

17. An implant as defined by claim 15 wherein said one-piece body further defines an elongated, generally flat, intramedullary stem extending generally perpendicular from said proximal surface.

18. An implant as defined by claim 12 wherein said body is fabricated from metal.

19. An implant as defined by claim 17 wherein said body is fabricated from titanium.

20. An implant as defined by claim 19 wherein said body is fabricated from a superalloy.

21. A wrist implant adapted to be secured to the radius at the radiocarpal joint to constrain ulnar movement of the proximal carpal row which includes the lunate bone, said implant comprising:
a member having a proximal surface and spaced palmar and dorsal sidewalls, said sidewalls joining to form a medial end wall and defining therewith an elongated, smooth, cup-shaped, concave carpal recess having a lunate surface, said recess and lunate surface being configured and dimensioned to receive, encircle and constrain at least a portion of the lunate bone and prevent ulnar migration of the carpal row; and
an intramedullary stem joined to said proximal surface of said member.

22. A wrist implant as defined by claim 21 wherein said member is generally wedge-shaped in dorsal and palmar plan views, said member tapering from said medial end wall to a lateral end.

23. A wrist implant as defined by claim 22 wherein said member has a generally teardrop shape in distal and proximal views.

24. A wrist implant as defined by claim 23 wherein said recess is elongated from said medial end to said lateral end.

25. A wrist implant as defined by claim 24 wherein said recess has a generally semicircular cross section.

26. A wrist implant as defined by claim 25 wherein said recess is undercut into said medial end wall to define a lunate surface.

27. A wrist implant adapted to be secured to the radius at the radiocarpal joint to constrain ulnar movement of the proximal carpal row, said implant comprising:
a member having a proximal surface and spaced palmar and dorsal sidewalls, said sidewalls joining to form a medial end wall and defining therewith a carpal recess having a lunate surface, said recess dimensioned to receive, encircle and constrain at least a portion of the lunate bone; and
an intramedullary stem joined to said proximal surface of said member, said member being generally wedge-shaped in dorsal and palmar plan views, said member tapering from said medial end wall to a lateral end, said member having a generally teardrop shape in distal and proximal views, said recess being elongated from said medial end to said lateral end, said recess having a generally semicircular cross section, said recess being undercut into said medial end wall to define a lunate surface and wherein said member and said stem are fabricated from metal.

28. A wrist implant as defined by claim 27 wherein said metal is titanium.

29. A wrist implant as defined by claim 28 wherein said metal is a superalloy.

* * * * *